(12) United States Patent
Root

(10) Patent No.: US 8,800,565 B1
(45) Date of Patent: Aug. 12, 2014

(54) BREATH INTAKE VALVE FOR A TRACHEOSTOMY TUBE

(76) Inventor: David H. Root, Penfield, NY (US)

(*) Notice: Subject to any disclaimer, the term of this patent is extended or adjusted under 35 U.S.C. 154(b) by 196 days.

(21) Appl. No.: 13/068,704

(22) Filed: May 18, 2011

Related U.S. Application Data

(60) Provisional application No. 61/395,802, filed on May 19, 2010.

(51) Int. Cl.
*A61M 11/00* (2006.01)

(52) U.S. Cl.
USPC ............ 128/207.16; 128/207.17; 128/207.15

(58) Field of Classification Search
USPC ............ 128/207.16, 207.17, 205.24, 201.28, 128/207.14, 207.12, 207.15
See application file for complete search history.

(56) References Cited

U.S. PATENT DOCUMENTS

| | | | | |
|---|---|---|---|---|
| 3,137,299 A * | 6/1964 | Tabor | ......................... | 128/207.16 |
| 3,844,290 A * | 10/1974 | Birch et al. | ............... | 128/207.16 |
| 3,952,335 A * | 4/1976 | Sorce et al. | ......................... | 623/9 |
| 4,040,428 A * | 8/1977 | Clifford | ................... | 128/207.16 |
| 4,054,153 A * | 10/1977 | Guyton | ........................... | 137/527 |
| 4,207,884 A * | 6/1980 | Isaacson | ................... | 128/200.24 |
| 4,538,607 A * | 9/1985 | Saul | .......................... | 128/207.16 |
| 4,582,058 A * | 4/1986 | Depel et al. | ............... | 128/207.17 |
| 4,759,356 A | 7/1988 | Muir | | |
| 5,048,518 A * | 9/1991 | Eliachar et al. | ........... | 128/207.14 |
| 5,059,208 A * | 10/1991 | Coe et al. | ............................ | 623/9 |
| 5,391,205 A * | 2/1995 | Knight | ............................... | 623/9 |
| 5,765,560 A * | 6/1998 | Verkerke et al. | ........... | 128/207.16 |
| 6,193,751 B1 * | 2/2001 | Singer | ................................ | 623/9 |
| 6,358,222 B1 * | 3/2002 | Grundei | ............................. | 604/9 |
| 6,668,831 B1 * | 12/2003 | Hegwood | .................. | 128/207.14 |
| 6,802,316 B1 * | 10/2004 | Fulgham | .................. | 128/207.14 |
| 6,971,382 B1 * | 12/2005 | Corso | ....................... | 128/200.26 |
| 7,025,784 B1 * | 4/2006 | Blom et al. | ........................ | 623/9 |
| 7,240,676 B2 * | 7/2007 | Rutter | ....................... | 128/207.16 |
| 7,370,654 B2 * | 5/2008 | Persson | .................... | 128/207.16 |
| 7,387,216 B1 * | 6/2008 | Smith | ......................... | 220/254.3 |
| 8,051,856 B2 * | 11/2011 | Bare et al. | ................ | 128/207.16 |
| 2005/0139266 A1 * | 6/2005 | Partridge | ................... | 137/527.8 |
| 2006/0266359 A1 * | 11/2006 | Van Beurden et al. | .. | 128/205.24 |
| 2007/0087309 A1 * | 4/2007 | Campion | ........................ | 433/141 |
| 2009/0194108 A1 * | 8/2009 | Newman, Jr. | ............. | 128/204.18 |
| 2012/0097168 A1 * | 4/2012 | Perez et al. | ............... | 128/207.15 |

\* cited by examiner

*Primary Examiner* — Steven Douglas

(57) ABSTRACT

A breath intake valve is connected to a tracheostomy tube inserted into a patient's trachea. The inner end of the valve attaches to the tracheostomy tube. An apertured disk endpiece with an O-ring around its circumference is releasably set into the outer end of the tubular valve body. A floppy diaphragm overlying the inner face of the disk endpiece functions as an intake valve to allow patient inhalation and air intake, and as a check valve to block patient exhalation, thereby to redirect it to the patient's larynx, sinuses, and mouth for normal speech. The O-ring gives way to forceful patient exhalation to release the disk endpiece from the tubular valve body. The disk endpiece is tethered to the breath intake valve body to prevent misplacement of the endpiece after such a release. The breath intake valve is itself likewise tethered to the tracheostomy tube to prevent its misplacement after any disconnection. The breath intake valve also includes a whistle to produce audible signal when exhalation is forceful.

13 Claims, 3 Drawing Sheets

BREATH INTAKE VALVE FOR A TRACHEOSTOMY TUBE

CROSS-REFERENCE TO RELATED APPLICATION

Priority is claimed under 35 U.S.C §119 from Provisional Patent Application No. 61/395,802, filed on May 19, 2010, by D. Root.

BACKGROUND OF THE INVENTION

This invention is a breath intake valve for a tracheostomy tube. Specifically, the invention is an improvement of the Tracheostomy Device shown and described in U.S. Pat. No. 4,759,356 to Muir.

A tracheotomy (or tracheostomy) involves placement of a breathing tube into an incision through the windpipe. The Muir patent relates to a "speaking" valve for the external free end of the breathing tube to assist a tracheostomy patient's speech. The Muir valve is a unidirectional air valve or check valve. It allows air intake into the patient's trachea, and it blocks exhalation, thereby redirecting exhaled air to the patient's larynx, epiglottis, sinuses, and mouth to permit normal speech.

SUMMARY OF THE INVENTION

In summary, this invention is a breath intake valve for connection with a tracheostomy tube inserted into a patient's trachea. The inner end of the valve attaches to the tracheostomy tube. An apertured disk endpiece with an O-ring around its circumference is releasably set into the outer end of the tubular valve body. A floppy diaphragm overlying the inner face of the disk endpiece functions as an intake valve to allow patient inhalation and air intake, and as a check valve to block patient exhalation, thereby to redirect it to the patient's larynx, sinuses, and mouth for normal speech. The O-ring gives way to forceful patient exhalation to release the disk endpiece from the tubular valve body. The disk endpiece is tethered to the tubular valve body to prevent its misplacement after such a release. The valve is itself likewise tethered to the tracheostomy tube to prevent its misplacement after any disconnection. The breath intake valve also includes a whistle to produce an audible signal when exhalation is forceful.

DRAWING

DESCRIPTION

Figure 1:
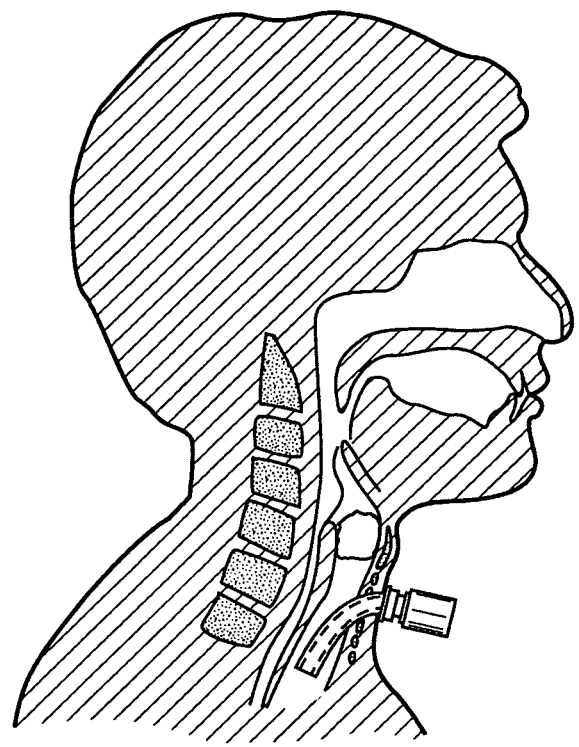
FIG. 1 represents a patient with a tracheostomy tube and associated breath intake valve.
Figure 2:
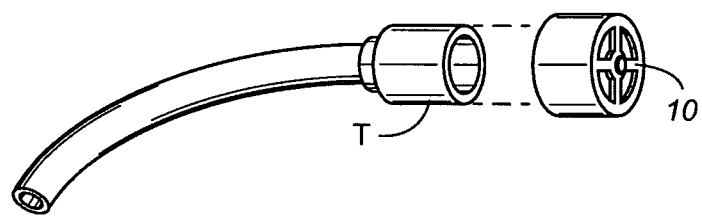
FIG. 2 is an exploded view of a prior art tracheostomy tube and associated breath intake valve.
Figure 3:
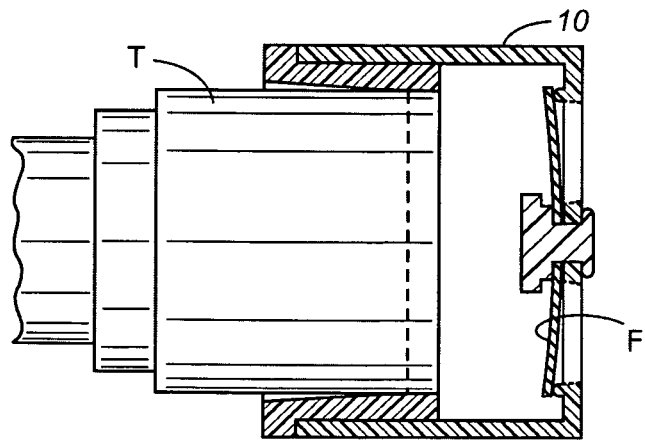
FIG. 3 is an enlarged sectional view of the breath intake valve of FIG. 2.

FIGS. 1-3 represent prior art. The component in FIGS. 1-3 which is relevant to this invention is the prior art breath intake valve 10. As the patient inhales, a valve flap F opens inward to allow inhalation through a breath intake tube T and into the patient. When the patient exhales, the valve flap F closes to prevent exhalation through the breath intake valve 10. Exhalation is instead directed up through the patient's larynx, epiglottis, sinuses, and mouth to enable the patient to speak. This is the desired respiration flow in a post-tracheostomy patient. However it is possible, and indeed has happened, that if the apparatus is improperly worn or incorrectly adjusted, the patient's exhalation can be totally blocked. Patients have fainted from this inability to exhale.

Figure 4:
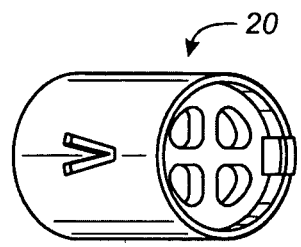
FIG. 4 shows a breath intake valve of this invention.
Figure 5:
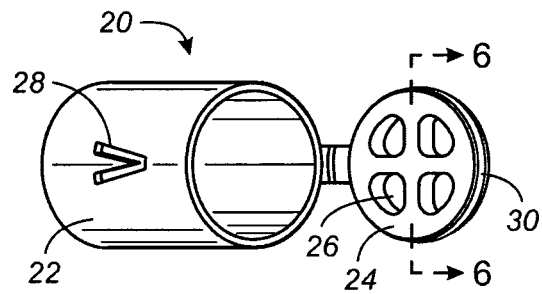
FIG. 5 shows the breath intake valve of FIG. 4 with its outer endpiece expelled.
Figure 6:
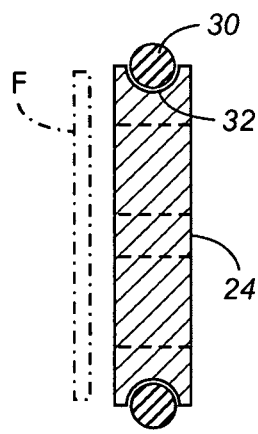
FIG. 6 is a sectional view of the intake valve endpiece, on the plane 6-6 of FIG. 5.

In FIGS. 4-6, a breath intake valve 20 of this invention includes a cylindrical body 22, a disk endpiece 24 with air apertures 26 through it, and a resilient valve flap F, similar to that in FIG. 3, disposed adjacent to the inner face of the disk endpiece 24. Inner and outer faces of the disk endpiece 24 are shown in FIG. 5 and FIG. 6 respectively. The valve flap F is shown somewhat schematically in FIG. 6; in reality it is mounted adjacent to the inner face of the disk endpiece 24. The endpiece 24 is releasably fit into the outer end of the tubular valve body 22 by an O-ring 30, and is hinged or otherwise tethered to it as shown in FIG. 5.

In normal operation the endpiece 24 remains in place (FIG. 4). If it becomes necessary to exhale through the valve 20, a deliberate exhalation will push the endpiece 24 open against a certain resistance provided by the O-ring 30. FIG. 5 shows the endpiece 24 in a break-open condition. The breath intake valve 20 (i.e. the combination valve body 22, endpiece 24, flap F, and O-ring 30) thus operates as an emergency relief valve.

FIG. 6 shows the endpiece 24 with a concave circumferential seat 32 for the O-ring 30, and a schematic representation of the valve flap F. "Deliberate exhalation" is meant as exhalation which is done consciously because it is done against some degree of resistance. Exhalation pressure required to release the endpiece is in the range of 10 to 20 centimeters of water. The O-ring 30 in a particular breath intake valve 20 is selected from among O-rings of different resilience, or of different minor radii, thereby to establish a desired endpiece release pressure suitable for case-by-case application. Different tracheostomy patients will require different endpiece release settings, depending on factors such as the patient's age, health, and strength.

The valve body 22 further includes a notch whistle 28 which sounds off when exhalation is attempted through the valve 20. This is a further safeguard to inform the patient that the system needs to be reset.

Figure 7:
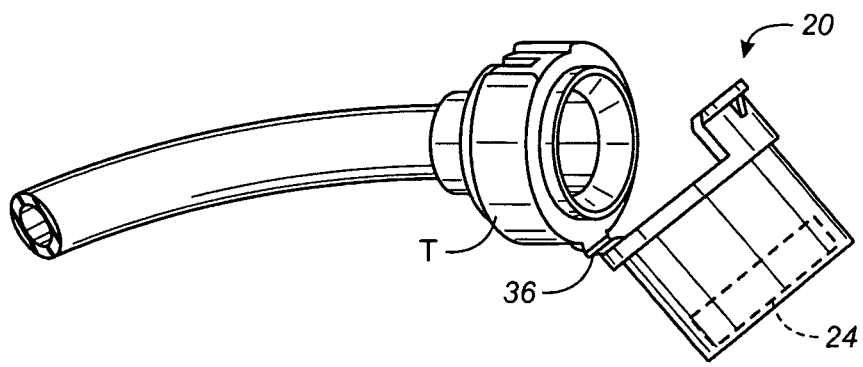
FIG. 7 is a view similar to FIG. 2 including a further improvement of this invention.

It may be necessary from time to time to remove the breath intake valve 20 from the intake tube T to permit a procedure such as suctioning of fluids from the patient. In such an event it is customary to remove the breath intake valve 20 from the tube T, and set it down wherever convenient while the procedure is performed. For convenience and cleanliness, I have hinged the breath intake valve 20 to the intake tube T, as indicated in FIG. 7. When it is necessary to remove the breath intake valve 20, it is not necessary to find a place to set it down. The valve drops out of the way to permit the procedure, but remains conveniently attached to the tube T by its hinge 36 to simplify its reconnection when the procedure is completed.

Figure 8:
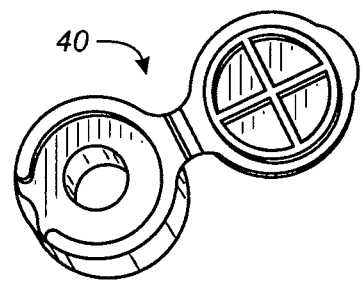
FIG. 8 shows a hinged cap for removable placement over the open end of the breath valve.

FIG. 8 shows a hinged cap 40 for removable placement over the end of the breath valve 20.

The foregoing description of a preferred embodiment of my invention is illustrative. The concept and scope of the invention are not limited by such details but only by the following claims.

What is claimed is:

1. A breath intake valve (20) for connection with a tracheostomy tube (T) inserted into a patient's trachea, said breath intake valve including:
   a tubular valve body (22) including an inner end for connection with said tracheostomy tube, and an outer end;
   an apertured disk endpiece (24) disposed within said outer end of said valve body (22), said disk endpiece (24) including a circumferential concave O-ring seat (32), and an O-ring disposed in said O-ring seat for sealing engagement with said tubular valve body (22);
   a breath intake valve flap (F) operatively connected to said disk endpiece (24) on the inner side thereof, said valve flap (F) being responsive to patient inhalation to open said disk endpiece for air intake through said tracheostomy tube (T) into the patient's trachea, and responsive to patient exhalation to close said disk endpiece to thereby redirect said exhalation to the patient's larynx, sinuses, and mouth for normal speech; and
   a hinge operatively associating the breath intake valve with the tracheostomy tube such that when removed from the valve body, the breath intake valve remains attached to the tracheostomy tube yet permitting access to an interior of the tracheostomy tube;
   said disk endpiece (24) and said O-ring responsive to exhalation pressure above a release pressure level to release said disk endpiece from said tubular body, thereby to permit exhalation through said intake valve (20).

2. The breath intake valve according to claim 1, said intake valve flap including a resilient diaphragm overlying said inner side of said endpiece.

3. The breath intake valve according to claim 1, said disk endpiece (24) being tethered to said tubular valve body (22) to prevent misplacement of said disk endpiece in an event of its release.

4. The breath intake valve according to claim 1, said tubular valve body (22) further including a notch whistle to produce an audible signal when exhalation is attempted through said breath intake valve.

5. The breath intake valve according to claim 1, said O-ring seat (32) being adapted to receive O-rings of different characteristics, thereby to modify said exhalation pressure release level to suit individual patients.

6. A breath intake valve (20) for connection with a tracheostomy tube (T) inserted into a patient's trachea, said breath intake valve including:
   a tubular valve body (22) including an inner end for connection with said tracheostomy tube, and an outer end;
   an apertured disk endpiece (24) disposed within said outer end of said valve body (22), said disk endpiece including a removable O-ring in an O-ring seat (32) around the outer circumference of said disk endpiece for circumferential engagement with the interior of said tubular valve body (22);
   a breath intake valve flap (F) operatively connected to said disk endpiece (24) on the inner side thereof, said valve flap being responsive to patient inhalation to open said disk endpiece for air intake to the patient through said tracheostomy tube, and responsive to patient exhalation to close said disk endpiece, thereby to redirect said exhalation to the patient's larynx, sinuses, and mouth;
   said disk endpiece and said O-ring being responsive to exhalation pressure above a preselected release pressure level to release said disk endpiece from said tubular body, thereby to permit exhalation through said valve (20), wherein said disk endpiece includes a circumferential O-ring seat suitable for receiving one of a plurality of O-rings having different characteristics and to thereby establish a desired endpiece release pressure for the breath intake valve.

7. The breath intake valve according to claim 6, said intake valve flap including a resilient diaphragm overlying said inner side of said endpiece.

8. The breath intake valve according to claim 6, said disk endpiece (24) being tethered to said tubular valve body (22) to prevent misplacement of said disk endpiece in an event of its release.

9. The breath intake valve according to claim 6, said tubular valve body (22) further including a notch whistle to produce an audible signal when exhalation is attempted through said breath intake valve.

10. The breath intake valve according to claim 6, said O-ring seat (32) being adapted to receive O-rings of different characteristics, thereby to modify said exhalation pressure release level to suit individual patients.

11. The breath intake valve according to claim 6, wherein the different characteristics of said O-ring include a different minor radii for each of said O-rings.

12. The breath intake valve according to in claim 6, wherein the different characteristics of said O-ring includes different O-ring resilience.

13. A method of avoiding pressure buildup and enabling deliberate exhalation in a tracheostomy patient having a tracheostomy tube inserted in a trachea, comprising:
   connecting a breath intake valve to the tracheostomy tube, said breath intake valve including:
      a tubular valve body including an inner end for connection with the tracheostomy tube, and an outer end;
      an apertured endpiece disposed within the outer end of said valve body, said endpiece including a removable O-ring in an O-ring seat adjacent the circumference of said endpiece, said O-ring engaging the interior of the tubular valve body;
      a breath intake valve flap operatively connected to said endpiece on an inner side thereof, said valve flap being responsive to the patient's inhalation to open for air intake to the patient through said tracheostomy tube, and to close in response to patient exhalation, thereby redirecting the exhalation to the patient's larynx;
      said disk endpiece and said O-ring responding to an exhalation pressure above a release pressure level to enable a release of said endpiece from said tubular body and permit exhalation through said intake valve; and
   installing an O-ring providing a desired endpiece release pressure for the patient on said O-ring seat.

* * * * *